United States Patent
Pfuetzner et al.

(10) Patent No.: US 8,383,585 B2
(45) Date of Patent: Feb. 26, 2013

(54) BIOMARKERS FOR CARDIODIABETES

(75) Inventors: Andreas Pfuetzner, Mainz (DE); Thomas Forst, Mainz (DE)

(73) Assignee: IKFE Institut fur Klinische Forschung und Entwicklung GmbH, Mainz (DE)

( * ) Notice: Subject to any disclaimer, the term of this patent is extended or adjusted under 35 U.S.C. 154(b) by 0 days.

(21) Appl. No.: 12/505,433

(22) Filed: Jul. 17, 2009

(65) Prior Publication Data

US 2010/0130404 A1     May 27, 2010

Related U.S. Application Data

(60) Provisional application No. 61/151,806, filed on Feb. 11, 2009, provisional application No. 61/081,645, filed on Jul. 17, 2008.

(51) Int. Cl.
   *A61K 38/00*    (2006.01)
   *A61K 38/28*    (2006.01)
   *A61K 35/14*    (2006.01)
   *C07K 1/00*    (2006.01)
   *G01N 33/543*    (2006.01)

(52) U.S. Cl. .......... 514/6.8; 514/6.9; 514/16.4; 514/5.9; 530/303; 530/380; 530/350; 436/518

(58) Field of Classification Search ........................ None
See application file for complete search history.

(56) References Cited

U.S. PATENT DOCUMENTS 7,723,050 B2 * 5/2010 Urdea et al. .................. 435/7.1
2007/0259377 A1 * 11/2007 Urdea et al. .................. 435/7.1

OTHER PUBLICATIONS

Bass (2008. Another Ginide: Where's the Beef, published at www.pipelinereview.com, downloaded from http://www.glgroup.com/News/Another-Glinide--Wheres-the-Beef--23072.html, Mar. 8, 2011).*

Pfutzner, A. and T. Forst (2006). "High-sensitivity C-reactive protein as cardiovascular risk marker in patients with diabetes mellitus." Diabetes Technol Ther 8(1): 28-36.

Pfutzner, A. et al., "Pioneer Study: PPARy Activation Results in Overall Improvement of Clinical and Metabolic Markers Associated with Insulin Resistance Independent of Long-Term Glucose Control." Horm. Metab. Res, 2005; 510-515.

Pfutzner, A. et al., "A Biomarker Concept for Assessment of Insulin Resistance, Beta-Cell Function and Chronic Systemic Inflammation in Type 2 Diabetes Mellitus," Clin. Lab., 2008; 54(11-12); 485-90.

* cited by examiner

*Primary Examiner* — Shulamith H Shafer
(74) *Attorney, Agent, or Firm* — Morgan, Lewis & Bockius LLP

(57) ABSTRACT

The invention provides compositions and methods for determining cardiodiabetes status in a subject. The invention also provides compositions and methods for treating a subject experiencing cardiodiabetes.

14 Claims, 1 Drawing Sheet

| Proinsulin high risk | adiponectin high | adiponectin medium | adiponectin low |
|---|---|---|---|
| hsCRP high | Yes: Glit & GLP-1/Ins<br>No: SU, Glin<br>possible: all others | Yes: Glit & GLP-1/Ins<br>No: SU, Glin<br>possible: all others | Yes: Glit & GLP-1/Ins<br>No: SU, Glin<br>possible: all others |
| hsCRP medium | Yes: Glit & GLP-1/Ins<br>No: SU, Glin<br>possible: all others | Yes: Glit & GLP-1/Ins/DPPIV<br>No: SU, Glin<br>possible: all others | Yes: Glit & GLP-1/Ins<br>No: SU, Glin<br>possible: all others |
| hsCRP low | Yes: Glit & GLP-1/Ins/DPPIV<br>No: SU, Glin<br>possible: all others | Yes: Glit & GLP-1/Ins/DPPIV<br>No: SU, Glin<br>possible: all others | Yes: Glit & GLP-1/Ins<br>No: SU, Glin<br>possible: all others |

| Proinsulin low risk | adiponectin high | adiponectin medium | adiponectin low |
|---|---|---|---|
| hsCRP high | Yes: Met&Glit/GLP-1/ DPPIV/Ins<br>No: SU, Glin<br>possible: all others | Yes: Met&Glit/GLP-1/ DPPIV/Ins<br>No: SU, Glin<br>possible: all others | Yes: Met&Glit/GLP-1/ DPPIV/Ins<br>No: SU, Glin<br>possible: all others |
| hsCRP medium | Yes: Met&Glit/DPPIV/Ins<br>possible: all classes | Yes: Met&Glit/DPPIV/Ins<br>possible: all classes | Yes: Met&Glit/GLP-1/ DPPIV/Ins<br>No: SU, Glin<br>possible: all others |
| hsCRP low | Yes: Met&Glit/DPPIV/Ins<br>possible: all classes | Yes: Met&Glit/DPPIV/Ins<br>possible: all classes | Yes: Met&Glit/GLP-1/ DPPIV/Ins<br>No: SU, Glin<br>possible: all others |

| | | |
|---|---|---|
| yes: | | recommended therapy (if no contraindications) |
| no: | | to be avoided, has negative impact |
| | possible: | drugs may be added if necessary for glucose lowering |

Legend:

| | |
|---|---|
| Glit: | Glitazone (Pioglitazone, Rosiglitazone) |
| GLP-1 | GLP-1 Analogue ( Exenatide, Liraglutide etc.) |
| DPPIV | DPPIV-Inhibitor (Sitagliptin, Vildagliptin, Saxagliptin) |
| Metf | Metformin |
| Glin | Glinides (Repaglinide, Nateglinide) |
| SU | Sulfonylurea (Gliclazide, Glimepiride etc.) |
| Acarb | Alpha-Glucosidase-Inhibitor (Acarbose) |
| all | all classes possible for glucose lowering |
| Ins | all types of insulin |
| RHI | regular human insulin |
| NPH | intermediate acting regular human insulin |
| (U)L | Zn-retarded insulins (lente, Ultralente) |
| SIA | Short-acting insulin analogue (Lispro, Aspart, Glulisine) |
| LIA | Long acting insulin analogue (Glargine, levemir) |

DB2/21232837.1

BIOMARKERS FOR CARDIODIABETES

CROSS-REFERENCE TO RELATED APPLICATIONS

This application claims under 35 USC 119(e) the benefit of U.S. Application 61/151,806, filed Feb. 11, 2009; and U.S. Application 61/081,645, filed Jul. 17, 2008, all of which are incorporated by reference in their entirety for all purposes.

FIELD OF THE INVENTION

The invention provides compositions and methods for determining cardiodiabetes status in a subject. The invention also provides compositions and methods for treating a subject experiencing cardiodiabetes.

BACKGROUND OF THE INVENTION

Metabolic syndrome comprises a number of components that have been associated with an increased risk of cardiovascular disease. One type of metabolic syndrome is referred to as insulin resistance syndrome or syndrome X, and is a cluster of risk factors that plays a role in cardiovascular disease morbidity among overweight and obese patients and those persons with type 2 diabetes mellitus. (See generally, Deen, *American Family Physician*, 2004, 69: 2875-2882.) A report from the National Cholesterol Education Program—Adult Treatment Panel (NCEP—ATP III) identified cardiodiabetes as an independent risk factor for cardiovascular disease.

Insulin resistance, abdominal obesity, high blood pressure and lipid disorders (i.e., elevated levels of triglycerides and low levels of high-density lipoprotein (HDL) cholesterol) are all characteristics indicative of cardiodiabetes. According to the NCEP—ATP III, a subject having any three of the above abnormalities is deemed to be afflicted with metabolic syndrome. Table 1 provides a summary of two different definitions for classifying a subject as having metabolic syndrome.

SUMMARY OF THE INVENTION

Patients with insulin resistance and β-cell dysfunction without elevation of blood glucose are not identified as suffering from diabetes mellitus. These normoglycemic patients, however, experience the same elevated cardiovascular risk, which is predominantly linked to vascular insulin resistance. This condition is newly referred to as "cardiodiabetes" or "cardiocardiodiabetes." The term "metabolic syndrome" may also be used herein to refer to this condition. A cardiodiabetic subject might not exhibit one or more of the normal symptoms of diabetes including, but not limited to, hyperglycemia, fatigue, unexplained weight loss, excessive thirst, excessive urination, excessive eating, poor wound healing, infections, altered mental status and blurry vision. A cardiodiabetic subject is at high risk for cardiovascular disease and may experience events such as myocardial infarction and stroke. That is, diabetes mellitus, cardiodiabetes and metabolic syndrome are phenotypes of a common underlying pathophysiology.

The cardiodiabetic patient population has experienced a worse outcome in previous epidemiological studies than those patients who are identified and treated as being diabetic. Classical laboratory biomarkers for diabetes cannot identify these cardiodiabetic patients. Because of pathophysiological considerations, surrogate markers for glucose metabolism may not be sufficient to describe the cardiovascular risk of patients with cardiodiabetes, and are not sufficient to describe this risk for cardiodiabetic patients.

The present provides compositions and methods for detecting and treating a disease, particularly cardiodiabetes, in a subject. A large number of biomarkers are known for a variety of metabolic, diabetic and cardiovascular conditions. See Publication US/2008/0057590, incorporated by reference in its entirety. However, it has been found that adiponectin, hsCRP, and intact proinsulin (and optionally leptin or other biomarkers, as outlined below) in combination are useful as biomarkers for cardiodiabetes, partly because, as discussed

TABLE 1

| Component | WHO diagnostic criteria (insulin resistance plus two of the following) | ATP III diagnostic criteria (three of the following) |
|---|---|---|
| Abdominal/central obesity | Waist to hip ratio: >0.90 (men), >0.85 (women), or BMI >30 kg per m$^2$ | Waist circumference: >102 cm (40 in) in men, >88 cm (35 in) in women |
| Hypertriglyceridemia | ≧150 mg per dL (≧1.7 mmol per L) | ≧150 mg per dL |
| Low HDL cholesterol | <35 mg per dL (<0.9 mmol per L) for men, <39 mg per dL (<1.0 mmol per L) for women | <40 mg per dL (<1.036 mmol per L) for men, <50 mg per dL (<1.295 mmol per L) for women |
| High blood pressure | ≧140/90 mm Hg or documented use of antihypertensive therapy | ≧130/85 mm Hg or documented use of antihypertensive therapy |
| High fasting glucose | Impaired glucose tolerance, impaired fasting glucose, insulin resistance, or diabetes | ≧110 mg per dL (≧6.1 mmol per L) |
| Microalbuminuria | Urinary albumin to creatinine ratio: 30 mg per g, or albumin excretion rate: 20 mcg per minute | |

(Reproduced from Deen, supra)

below, each allows the assessment of a different aspect of disease. Each of these biomarkers alone does not lead to an overall understanding of a subject's risk of experiencing cardiodiabetes. For example, suppressed adiponectin levels by themselves could indicate a disease state, but not necessarily. Determining that a subject's adiponectin level is suppressed and hsCRP level is elevated may to some extent suggest cardiodiabetes, but not with the greatest certainty. Further determining that a subject's level of intact proinsulin is elevated allows the practitioner to conclude that the subject has a 200% elevated risk of cardiovascular disease. Thus, measuring adiponectin, hsCRP and intact proinsulin provides the maximum amount of information concerning the disease state of a subject through a minimum number of biomarkers. Adiponectin, hsCRP and intact proinsulin also have the practical advantage of being physically stable markers. This allows samples to be collected and measured later, for example, in batches, or alternatively that no special handling of the samples (such as immediate freezing, for example) need be used.

Accordingly, the present invention provides compositions and methods for the detection and/or quantification of a set of particular biomarkers (including, but not limited to, any combination of adiponectin, hsCRP and intact proinsulin, as well as combinations including leptin and/or other markers discussed below) that allow for determining cardiodiabetes in a subject. Without such determination, treatment, and thus reduction of serious cardiovascular events, might not otherwise occur.

The invention also provides for selection of efficient risk-reducing treatment and therapies to avoid cardiovascular complications. The invention provides biological markers that in various combinations can be used in methods to monitor subjects that are undergoing therapies affecting cardiodiabetes. Indications of cardiodiabetes allow a caregiver to select or modify therapies or interventions for treating subjects. A number of drugs for the treatment of diabetes have been developed and are available on the market. The biomarkers disclosed herein allow for determining a subject's level of response to drugs such as antidiabetes drugs or other drugs described herein, and for monitoring the effectiveness of drug treatment. The present invention is particularly directed to the use of a minimum number of biomarkers to provide a maximum amount of information concerning the disease status of a subject.

A panel of biomarkers consisting of adiponectin, hsCRP, intact proinsulin (and optionally leptin or other biomarkers, as outlined below) may optionally be combined with measurements of other biomarkers to assess cardiodiabetes.

In current practice, the standard of care is to administer drugs that nonspecifically reduce symptoms. As these interventions fail in later stages, more intensive approaches are pursued leading to use of insulin and multiple pharmacotherapy; by then, attempting to treat the underlying pathophysiology may be ineffective. Thus, the invention also provides a number of drugs and drug combinations that may be administered to a subject to treat a disease. Through the compositions and methods of the present invention, subjects may be treated with drugs or drug combinations that not only provide targeted symptom improvement, but also improve a subject's overall disease state.

The invention further provides methods for determining the unsuitability of certain drug therapies. That is, depending on measurements of a biomarker panel, a number of drugs and drug combinations that are not or should not be administered to a subject to treat cardiodiabetes. The literature in some instances discloses the administration of certain drugs to a subject whose biomarker levels satisfy certain criteria as disclosed herein, whereas according to the present invention, these subjects are not or should not be administered these drugs.

Often, subjects may exhibit normal glucose levels but nonetheless experience β-cell dysfunction, insulin resistance, systemic inflammation and lipostatis. The invention thus provides for early detection of subjects with normoglycemic vascular insulin resistance at high risk for myocardial infarction and stroke.

In one aspect, the invention provides a composition comprising a solid support comprising: (a) a capture binding ligand selective for adiponectin, (b) a capture binding ligand selective for hsCRP, and (c) a capture binding ligand selective for intact proinsulin.

In one embodiment, one of the capture binding ligands comprises an antibody.

In one embodiment, the composition further comprises: (a) a soluble capture ligand selective for adiponectin, (b) a soluble capture ligand selective for hsCRP, and (c) a soluble capture ligand selective for intact proinsulin.

In one embodiment, each of the soluble capture ligands comprises a detectable marker.

In one embodiment, a detectable marker is a fluorophore.

In one embodiment, a detectable marker is a conjugated enzyme.

In one embodiment, the conjugated enzyme is horseradish peroxidase.

In one embodiment, the composition further comprises a detector.

In one aspect, the invention provides a method of treating a cardiodiabetes in a subject comprising (a) measuring the concentration of a biomarker panel in a sample from the subject, the biomarker panel consisting of adiponectin, hsCRP and intact proinsulin; and (b) effecting a therapy with respect to the subject.

In one embodiment, if the risk level associated with each of the concentrations of adiponectin, hsCRP and intact proinsulin respectively is selected from (a) high, high and high; (b) high, medium and high; (c) medium, high and high; (d) low, high and high; (e) low, medium and high; and (f) low, low and high, then the subject is administered a glitazone and a drug or combination of drugs selected from a GLP-1 analog and an insulin.

In one embodiment, if the risk level associated with each of the concentrations of adiponectin, hsCRP and intact proinsulin respectively is selected from (a) high, low and high; (b) medium, medium and high; and (c) medium, low and high, then the subject is administered a glitazone and a drug or combination of drugs selected from a GLP-1 analog, an insulin and a DPPIV inhibitor.

In one embodiment, if the risk level associated with each of the concentrations of adiponectin, hsCRP and intact proinsulin respectively is selected from (a) high, high and low; (b) medium, high and low; (c) low, high and low; (d) low, medium and low; and (e) low, low and low, then the subject is administered metformin and a drug or combination of drugs selected from a glitazone, a GLP-1 analog, a DPPIV inhibitor and an insulin.

In one embodiment, if the risk level associated with each of the concentrations of adiponectin, hsCRP and intact proinsulin respectively is selected from (a) high, medium and low; (b) high, low and low; (c) medium, medium and low; and (d) medium, low and low, then the therapy comprises administering metformin and a drug or combination of drugs selected from a glitazone, a DPPIV inhibitor and an insulin.

In one embodiment, the subject is not administered a drug or combination of drugs selected from a sulfonylurea and a glinide.

In one embodiment, the subject is administered one or more additional drugs comprising one or more glucose lowering drugs.

In one embodiment, a sample comprises blood.

In one embodiment, the method further comprises taking a measurement of at least one additional biomarker.

In one embodiment, the additional biomarker is selected from the group consisting of leptin, mRNAx, NFκB, IL-6, MMP-9, TNFα, NFκB, eNOS, PPARγ, MCP-1, PAI-1, ICAM/VCAM, E-selectin, P-selectin, von Willebrand factor, sCD40L, insulin, glucose, HbA1c, free fatty acids, triglycerides, VLDL, small dense LDL, oxidized LDL, resistin, HDL, NO, IκB-α, IκB-β, p105, RelA, TNFα, MIF, inflammatory cytokines and molecules involved in signaling pathways.

In one embodiment, the additional biomarker is MMP-9.

In one embodiment, the concentration of intact proinsulin, hsCRP and adiponectin in the sample is measured and each is a high risk concentration.

In one embodiment, the additional biomarker is leptin.

In one embodiment, the method comprises contacting the sample with a composition of invention.

In one aspect, the invention provides use of a composition of the invention to determine a therapy for a subject experiencing cardiodiabetes.

In one embodiment, the use comprises contacting the composition with a sample from the subject and measuring the concentrations of adiponectin, hsCRP and intact proinsulin.

In one embodiment, if the risk level associated with each of the concentrations of adiponectin, hsCRP and intact proinsulin respectively is selected from (a) high, high and high; (b) high, medium and high; (c) medium, high and high; (d) low, high and high; (e) low, medium and high; and (f) low, low and high, then the therapy comprises administering a glitazone and a drug or combination of drugs selected from a GLP-1 analog and an insulin.

In one embodiment, if the risk level associated with each of the concentrations of adiponectin, hsCRP and intact proinsulin respectively is selected from (a) high, low and high; (b) medium, medium and high; and (c) medium, low and high, then the therapy comprises administering glitazone and a drug or combination of drugs selected from a GLP-1 analog, an insulin and a DPPIV inhibitor.

In one embodiment, if the risk level associated with each of the concentrations of adiponectin, hsCRP and intact proinsulin respectively is selected from (a) high, high and low; (b) medium, high and low; (c) low, high and low; (d) low, medium and low; and (e) low, low and low, then the therapy comprises administering metformin and a drug or combination of drugs selected from a glitazone, a GLP-1 analog, an DPPIV inhibitor and an insulin.

In one embodiment, if the risk level associated with each of the concentrations of adiponectin, hsCRP and intact proinsulin respectively is selected from (a) high, medium and low; (b) high, low and low; (c) medium, medium and low; and (d) medium, low and low, then the therapy comprises administering metformin and a drug or combination of drugs selected from a glitazone, a DPPIV inhibitor and an insulin.

In one embodiment, the therapy comprises not administering a drug or combination of drugs selected from a sulfonylurea and a glinide.

In one embodiment, the therapy further comprises administering one or more additional glucose lowering drugs.

In one aspect, the invention provides a method of determining whether a subject belongs to a population that would benefit from a therapy, the method comprising contacting a sample from the subject with a composition of the invention; and measuring the concentrations of adiponectin, hsCRP and intact proinsulin in the sample.

In one embodiment, the therapy comprises administering a glitazone and a drug or combination of drugs selected from a GLP-1 analog and an insulin, and wherein if the risk level associated with each of the concentrations of adiponectin, hsCRP and intact proinsulin respectively is selected from (a) high, high and high; (b) high, medium and high; (c) medium, high and high; (d) low, high and high; (e) low, medium and high; and (f) low, low and high.

In one embodiment, the therapy comprises administering a glitazone and a drug or combination of drugs selected from a GLP-1 analog, an insulin and a DPPIV inhibitor, and wherein the risk level associated with each of the concentrations of adiponectin, hsCRP and intact proinsulin respectively is selected from (a) high, low and high; (b) medium, medium and high; and (c) medium, low and high.

In one embodiment, the therapy comprises administering metformin and a drug or combination of drugs selected from a glitazone, a GLP-1 analog, a DPPIV inhibitor and an insulin, and wherein the risk level associated with each of the concentrations of adiponectin, hsCRP and intact proinsulin respectively is selected from (a) high, high and low; (b) medium, high and low; (c) low, high and low; (d) low, medium and low; and (e) low, low and low.

In one embodiment, the therapy comprises administering metformin and a drug or combination of drugs selected from a glitazone, a DPPIV inhibitor and an insulin, and wherein (a) high, medium and low; (b) high, low and low; (c) medium, medium and low; and (d) medium, low and low.

In one embodiment, the therapy does not comprise administering a drug or combination of drugs selected from a sulfonylurea and a glinide.

In one embodiment, the therapy further comprises administering one or more additional glucose lowering drugs.

BRIEF DESCRIPTION OF THE DRAWINGS

FIG. 1 shows a therapy decision matrix for a biomarker panel that includes adiponectin, hsCRP and intact proinsulin. The symbol "&" means "and" and "/" means "or." Specific drugs are provided as non-limiting examples.

DESCRIPTION OF EMBODIMENTS

Biomarkers

Biomarkers may originate from epidemiological studies, animal studies, pathophysiological considerations and end-organ experiments. Ideally, a biomarker will have a high predictive value for a meaningful outcome measure, can be or is validated in appropriately designed prospective trials, reflects therapeutic success by corresponding changes in the surrogate marker results, and should be easy to assess in clinical practice.

The term "surrogate marker," "biomolecular marker," "biomarker" or "marker" (also sometimes referred to herein as a "target analyte," "target species" or "target sequence") refers to a molecule whose measurement provides information as to the state of a subject. In various exemplary embodiments, the biomarker is used to assess a pathological state. Measurements of the biomarker may be used alone or combined with other data obtained regarding a subject in order to determine the state of the subject. In one embodiment, the biomarker is "differentially present" in a sample taken from a subject of one phenotypic status (e.g., having a disease) as compared with another phenotypic status (e.g., not having the disease). In one embodiment, the biomarker is "differentially present" in a sample taken from a subject undergoing no therapy or one type of therapy as compared with another type of therapy. Alternatively, the biomarker may be "differentially present" even if there is no phenotypic difference, e.g. the biomarkers may allow the detection of asymptomatic risk. A biomarker may be determined to be "differentially present" in a variety of ways, for example, between different phenotypic statuses if the mean or median level (particularly the expression level of the associated mRNAs as described below) of the biomarker in the different groups is calculated to be statistically significant. Common tests for statistical significance include, among others, t-test, ANOVA, Kruskal-Wallis, Wilcoxon, Mann-Whitney and odds ratio.

As described herein, a biomarker may be, for example, a small molecule, an analyte or target analyte, a lipid (including glycolipids), a carbohydrate, a nucleic acid, a protein, any derivative thereof or any and all combinations of these molecules, with proteins and nucleic acids finding particular use in the invention. As will be appreciated by those in the art, a large number of analytes may be detected using the present methods; basically, any biomarker for which a binding ligand, described below, may be made may be detected using the methods of the invention.

In various embodiments, the biomarkers used in the panels of the invention can be detected either as proteins or as nucleic acids (e.g. mRNA or cDNA transcripts) in any combination. In various embodiments, the protein form of a biomarker is measured. As will be appreciated by those in the art, protein assays may be done using standard techniques such as ELISA assays. In various embodiments, the nucleic acid form of a biomarker (e.g., the corresponding mRNA) is measured. In various exemplary embodiments, one or more biomarkers from a particular panel are measured using a protein assay and one or more biomarkers from the same panel are measured using a nucleic acid assay.

As will be appreciated by those in the art, there are a large number of possible proteinaceous target analytes and target species that may be detected using the present invention. The term "protein," "polypeptide" or "oligopeptide" refers to at least two or more peptides or amino acids joined by one or more peptide bonds. The term "protein" includes "peptide." A protein or an amino acid may be naturally or nonnaturally occurring and may be also be an analog, a derivative or a peptidomimetic structure. The term "protein" refers to wild-type sequences, variants of wild-type sequences and either of these containing analogs or derivatized amino acids. Examples of derivatized amino acids include, without limitation, those that have been modified by the attachment of labels (described below); acetylation; acylation; ADP-ribosylation; amidation; covalent attachment of flavin, a heme moiety, a nucleotide, a lipid or phosphatidylinositol; cross-linking; cyclization; disulfide bond formation; demethylation; esterification; formation of covalent crosslinks, cystine or pyroglutamate; formylation; gamma carboxylation; glycosylation; GPI anchor formation; hydroxylation; iodination; methylation; myristoylation; oxidation; proteolytic processing; phosphorylation; prenylation; racemization; selenoylation; sulfation; and ubiquitination. Such modifications are well-known to those of skill in the art and have been described in great detail in the scientific literature. Several particularly common modifications such as glycosylation, lipid attachment, sulfation, gamma-carboxylation, hydroxylation and ADP-ribosylation, for instance, are described in basic texts, such as Creighton, *Proteins—Structure and Molecular Properties,* 2d ed. (New York: W. H. Freeman and Company, 1993). Many detailed reviews are available on this subject, such as in Johnson, ed., *Posttranslational Covalent Modification of Proteins* (New York: Academic Press, 1983); Seifter et al., *Meth. Enzymol.,* 1990, 182: 626-646; and Rattan et al., *Ann. N.Y. Acad. Sci.,* 1992, 663: 48-62. A variant may contain one or more additions, deletions or substitutions of one or more peptides compared to wild-type or a different variant sequence. The sidechains of a protein may be in either the (R) or the (S) configuration. In a preferred embodiment, the amino acids are in the (S) or (L)-configuration. As discussed below, when the protein is used as a binding ligand, it may be desirable to utilize protein analogs to retard degradation by sample contaminants.

In various embodiments, variants of the sequences described herein, including proteins and nucleic acids based on e.g. splice variants, variants comprising a deletion, addition, substitution, fragments, preproprotein, processed preproprotein (e.g. without a signaling peptide), processed protein (e.g. resulting in an active form), nonhuman sequences and variant nonhuman sequences may be used as biomarkers.

In various exemplary embodiments, the biomarker is a nucleic acid. The term "nucleic acid" or "oligonucleotide" or grammatical equivalents herein means at least two nucleotides covalently linked together. A nucleic acid of the present invention will generally contain phosphodiester bonds, although in some cases, as outlined below, for example in the use of binding ligand probes, nucleic acid analogs are included that may have alternate backbones, comprising, for example, phosphoramide (Beaucage et al., *Tetrahedron,* 49(10): 1925 (1993) and references therein; Letsinger, *J. Org. Chem.* 35: 3800 (1970); Sprinzl et al., *Eur. J. Biochem.* 81:579 (1977); Letsinger et al., *Nucl. Acids Res.* 14: 3487 (1986); Sawai et al, *Chem. Lett.* 13(5): 805 (1984); Letsinger et al., *J. Am. Chem. Soc.* 110:4470 (1988); and Pauwels et al., *Chemica Scripta* 26:141 (1986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach,* (Oxford University Press, 1991), and peptide nucleic acid backbones and linkages (see Egholm, *J. Am. Chem. Soc.* 114: 1895 (1992); Meier et al., *Chem. Int. Ed. Engl.* 31: 1008 (1992); Nielsen, *Nature,* 365: 566 (1993); Carlsson et al., *Nature,* 380: 207 (1996), all of which are incorporated by reference). Other analog nucleic acids include those with positive backbones (Denpcy et al., *Proc. Natl. Acad. Sci. USA* 92: 6097 (1995)), non-ionic backbones (U.S. Pat. Nos. 5,386,023; 5,637,684; 5,602,240; 5,216,141 and 4,469,863; Kiedrowski et al., *Angew. Chem. Intl. Ed. English* 30: 423 (1991); Letsinger et al., *J. Am. Chem. Soc.* 110: 4470 (1988); Letsinger et al., *Nucleoside & Nucleotide* 13: 1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4: 395 (1994); Jeffs et al., *J. Biomolecular NMR* 34: 17 (1994); and Horn et al., *Tetrahedron Lett.* 37: 743 (1996)) and non-ribose backbones, including those described in U.S. Pat. Nos. 5,235,033 and 5,034, 506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.,* 24: 169-176 (1995)). Several nucleic acid analogs are described in Rawls, *C & E News,* 35 (Jun. 2, 1997). All of these references are hereby expressly incorporated by reference. These modifications of the ribose-phosphate backbone may be done to increase the stability and half-life of such molecules in physiological environments. As will be appreciated by those in the art, all of these nucleic acid analogs may find use in the present invention. In addition, mixtures of naturally occurring nucleic acids and analogs can be made.

It has been found that assays for cardiodiabetes involving the measurements of adiponectin, hsCRP and proinsulin has greater value in determining cardiodiabetes than any of these biomarkers alone. This particular combination of biomarkers allows attainment of clinically useful sensitivity and specificity, and the detection and staging of less severe cases of a disease that modulates cardiodiabetes. Accordingly, measurements of a biomarker panel comprising or consisting of adiponectin, hsCRP and proinsulin may be used to improve the sensitivity and/or specificity of a diagnostic test compared to a test involving any one of these biomarkers alone.

Adiponectin

In various embodiments, adiponectin is used as a biomarker. Adiponectin values are useful as a predictive biomarker for insulin resistance and as a monitoring tool in the treatment of insulin resistance related disorders. Full-length adiponectin (f-Ad) is a 30 kDa serum protein specifically secreted by adipocytes. (See for example, GenBank Accession No. BAA08227 incorporated by reference.) Adiponectin typically circulates in human blood at concentrations ranging between 5 and 12 mg/L, thus accounting for approximately 0.01% of total plasma protein. Schondorf et al., *Clin. Lab.*, 2005, 51: 489-494. Adiponectin levels have higher median values in females (about 8.7 mg/L) than in males (about 5.5 mg/L), and may be affected by age as well. Adiponectin levels correlate negatively with BMI, visceral fat mass and insulin levels. Accordingly, adiponectin is decreased in obese subjects and in patients suffering from type 2 diabetes, macroangiopathy or other metabolic disorders. The lowest adiponectin values have been found in obese patients with both type 2 diabetes and coronary heart disease. Tables 2A and 2B show two different categorization of various adiponectin concentrations in relation to risk of arteriosclerosis and insulin resistance.

TABLE 2A

| Adiponectin Concentration (mg/L) | Risk Level for Arteriosclerosis and Insulin Resistance |
|---|---|
| >10 | low |
| 7-10 | medium |
| <7 | high |

TABLE 2B

| Adiponectin Concentration (mg/L) | Risk Level for Arteriosclerosis and Insulin Resistance |
|---|---|
| >10 | low |
| 7-10 | medium |
| 4-7 | high |
| <4 | very high |

A number of compounds have been shown to affect adiponectin levels in a subject. Pfiitzner et al., *Diabetes, Stoffwechsel and Herz*, 2007, 16: 91-97 have shown that sulfonylurea, metformin, thiazolidinedione, metformin+sulfonylurea, metformin+thiazolidinedione, sulfonylurea+glitazone, and metformin+sulfonylurea+thiazolidinedione may have an effect on adiponectin levels. Thus, in one embodiment, any of these compounds or combinations may be administered to a subject.

Accordingly, suitable capture binding ligands, as further discussed herein, for detection and/or quantification of adiponectin include, but are not limited to, antibodies that are selective for adiponectin. Adiponectin antibodies are known and commercially available. In an exemplary embodiment, adiponectin has a peptide sequence according to GenBank Accession No. BAA08227 or is derived from a nucleic acid sequence according to GenBank Accession No. D45371.

High Sensitivity C-Reactive Protein (hsCRP)

In various embodiments, CRP (C-reactive protein) or hsCRP (high sensitivity C-reactive protein) is used as a biomarker. CRP is a member of the pentraxin family, comprising five noncovalently associated protomers arranged symmetrically around a central pore and has a molecular weight of 118,000 Da. (See generally, Jialal et al., *Hypertension*, 2004, 44: 6-11) CRP is a marker of inflammation that has been shown to predict incident myocardial infarction, stroke, peripheral arterial disease, and sudden cardiac death process. Ridker, *Circulation*, 2003, 107: 363-369. Various epidemiological studies involving individuals with no prior history of cardiovascular disease have shown that a single, non-fasting measure of CRP is a strong predictor of future vascular events. The predictive value of CRP has proven independent of major traditional risk factors, such as age, smoking, cholesterol levels, blood pressure and diabetes.

Table 3 shows ranges of hsCRP that are correlated with various cardiovascular risk levels.

TABLE 3

| hsCRP Concentration (mg/L) | Cardiovascular Risk Level |
|---|---|
| 0-1 | low |
| >1-3 | moderate |
| >3-10 | high |
| >10 | unspecific elevation; not interpretable |

High-sensitivity CRP assays have been developed and are now widely available. (Roberts et al., *Clinical Chemistry* 2001, 47: 444-450.) In one embodiment, a biomarker, such as hsCRP, is measured by immune turbidometry.

Accordingly, suitable capture binding ligands, as further discussed herein, for detection and/or quantification of hsCRP include, but are not limited to, antibodies that are selective for hsCRP. hsCRP antibodies are known and commercially availableIn an exemplary embodiment, hsCRP has a peptide sequence according to GenBank Accession No. AAA52075 or is derived from a nucleic acid sequence according to GenBank Accession No. M11725.

Intact Proinsulin

In various embodiments, intact proinsulin is used as a biomarker. As used herein, "proinsulin" refers to the prohormone precursor to insulin made in the β-cell of the islets of Langerhans. Proinsulin may be cleaved within β-cell granules to result in two separate molecules: C-peptide and insulin. Partial processing of proinsulin may result in split or "des" forms of proinsulin. (Clark, *Ann Clin Biochem*, 1999, 36: 541-564.) The term "proinsulin" as used herein preferably refers to the unprocessed form of proinsulin, that is, "intact proinsulin."

Intact proinsulin concentrations are related to atherosclerosis and cardiovascular disease. If the demand for insulin triggered by insulin resistance reaches a certain threshold, insufficient cleavage capacity of β-cell carboxypeptidase H leads to an increased secretion of intact proinsulin in addition to the desired insulin molecule. Intact proinsulin, however, has been demonstrated to be an independent cardiovascular risk factor. Assessment of β-cell function by determination of intact proinsulin facilitates the selection of the most promising therapy and also serves to monitor treatment success in the further course of the disease. Intact proinsulin may serve as a marker to investigate β-cell function and allows for a secretion-oriented staging of type 2 diabetes. Table 4 shows the correlation between intact proinsulin concentration and β-cell function.

TABLE 4

| Intact Proinsulin Concentration (pmol/L) | Risk Level of β-cell Dysfunction |
|---|---|
| >11 | high |
| ≦11 | low |

Table 4 shows that for intact proinsulin concentrations of ≦11 pmol/L, β-cell function can be characterized as good, while for intact proinsulin concentrations of >11 pmol/L, β-cell function can be characterized as bad.

Chemiluminescence is one technique that can be used to measure intact proinsulin and other biomarkers. Two types of chemiluminescence assays are able to specifically measure uncleaved "intact" proinsulin and "total" proinsulin (proinsulin and its specific and non-specific degradation products) in human plasma (MLT Intact Proinsulin and MLT Total Proinsulin; Sciema, Mainz, Germany). Other methods suitable for proinsulin include without limitation chromatography, particularly HPLC, stable isotope dilution mass spectrometry assays, and ELISA. See, generally, Clark.

Accordingly, suitable capture binding ligands, as further discussed herein, for detection and/or quantification of proinsulin include, but are not limited to, antibodies that are selective for proinsulin. Intact proinsulin antibodies are known and commercially available. In an exemplary embodiment, intact proinsulin has a peptide sequence according to GenBank Accession No. AAA72531 or is derived from a nucleic acid sequence according to GenBank Accession No. M12913.

Leptin

In various embodiments, leptin is used as a biomarker. Leptin is a 16 kDa adipose-derived protein hormone that plays a role in regulating energy intake and energy expenditure, including appetite and metabolism. Leptin, acting through the leptin receptor, is part of a signaling pathway that can inhibit food intake or regulate energy expenditure to maintain constancy of the adipose mass. Leptin also has several endocrine functions, and is involved in the regulation of immune and inflammatory responses, hematopoiesis, angiogenesis and wound healing. Mutations in the leptin gene and/or its regulatory regions cause severe obesity, and morbid obesity with hypogonadism. Leptin has also been linked to type 2 diabetes mellitus development. Tables 5A and 5B show various disease risk levels associated with various concentrations of leptin in a sample taken from a human subject.

TABLE 5A

| Leptin Concentration (adult male) (ng/mL) | Disease Risk Level |
|---|---|
| >30 | high |
| 20-30 | medium |
| <20 | low |

TABLE 5B

| Leptin Concentration (adult female) (ng/mL) | Disease Risk Level |
|---|---|
| >60 | high |
| 40-60 | medium |
| <40 | low |

Accordingly, suitable capture binding ligands, as further discussed herein, for detection and/or quantification of leptin include, but are not limited to, antibodies that are selective for leptin. Leptin antibodies are known and commercially available. In an exemplary embodiment, leptin has a peptide sequence according to RefSeq Accession No. NP_000221 or is derived from a nucleic acid sequence according to RefSeq Accession No. NM_000230.

Biomarker Panels

Any combination of the biomarkers described herein is used to assemble a biomarker panel, which is detected or measured as described herein. As is generally understood in the art, a combination may refer to an entire set or any subset or subcombination thereof. The term "biomarker panel," "biomarker profile," or "biomarker fingerprint" refers to a set of biomarkers. As used herein, these terms can also refer to any form of the biomarker that is measured. Thus, if adiponectin is part of a biomarker panel, then either adiponectin protein or adiponectin mRNA, for example, could be considered to be part of the panel. While individual biomarkers are useful as diagnostics, it has been found that a combination of biomarkers can sometimes provide greater value in determining a particular status than single biomarkers alone. Specifically, the detection of a plurality of biomarkers in a sample can increase the sensitivity and/or specificity of the test. Thus, in various embodiments, a biomarker panel may include 1, 2, 3, 4, 5, 6, 7, 8, 9, 10 or more types of biomarkers. In various exemplary embodiments, the biomarker panel consists of a minimum number of biomarkers to generate a maximum amount of information. Thus, in various embodiments, the biomarker panel consists of 3, 4, 5, 6, 7 or 8 types of biomarkers. Where a biomarker panel "consists of" a set of biomarkers, no biomarkers other than those of the set are present. In exemplary embodiments, the biomarker panel consists of 3 biomarkers disclosed herein. In various embodiments, the biomarker panel consists of 4 biomarkers disclosed herein.

In various exemplary embodiments, the biomarker panel comprises adiponectin, hsCRP and proinsulin. In various exemplary embodiments, the biomarker panel comprises any combination of adiponectin, hsCRP and proinsulin. In various exemplary embodiments, the biomarker panel consists of adiponectin, hsCRP and proinsulin. In various exemplary embodiments, the biomarker panel consists of any combination of adiponectin, hsCRP and proinsulin. In various exemplary embodiments, the biomarker panel consists of 2 biomarkers selected from adiponectin, hsCRP and proinsulin. In various exemplary embodiments, the protein form of adiponectin, hsCRP and proinsulin is detected using a protein assay as known in the art or discussed herein.

In various exemplary embodiments, the biomarker panel comprises or consists of adiponectin, hsCRP and proinsulin and 1, 2, 3, 4 or more additional biomarkers. Such additional biomarkers may, for example, increase the specificity and/or sensitivity the test. Additional biomarkers suitable for biomarker panels include, without limitation, any combination of biomarkers selected from leptin, mRNAx, NFκB, IL-6, MMP-9, TNFα, NFκB, eNOS, PPARγ, MCP-1, PAI-1, ICAM/VCAM, E-selectin, P-selectin, von Willebrand factor, sCD40L, insulin, glucose, HbA1c, free fatty acids, triglycerides, VLDL, small dense LDL, oxidized LDL, resistin, HDL, NO, IκB-α, IκB-β, p105, RelA, TNFα, MIF, inflammatory cytokines, molecules involved in signaling pathways and any biomarkers disclosed in US Publication US/2008/0057590. It should be understood that in this embodiment, the biomarker panel can include any combination of adiponectin, hsCRP, proinsulin and the remainder of these markers. In various exemplary embodiments, the biomarker panel comprises adiponectin, hsCRP, proinsulin and leptin. In various exemplary embodiments, the biomarker panel comprises any combination of adiponectin, hsCRP, proinsulin and leptin. In various exemplary embodiments, the biomarker panel consists of adiponectin, hsCRP, proinsulin and leptin. In various exemplary embodiments, the biomarker panel consists of any combination of adiponectin, hsCRP, proinsulin and leptin. In various exemplary embodiments, the biomarker panel consists of 2 or 3 biomarkers selected from adiponectin, hsCRP, proinsulin and leptin. In various exemplary embodiments, the biomarker panel comprises or consists of adiponectin, hsCRP, proinsulin, leptin and 1, 2, 3, 4 or more additional biomarkers.

The term "clinical parameter" refers to all non-sample or non-analyte biomarkers of subject health status or other characteristics, such as, without limitation, age, ethnicity, gender, diastolic blood pressure and systolic blood pressure, family history, height, weight, waist and hip circumference, body-mass index, as well as others such as Type I or Type II Diabetes Mellitus or Gestational Diabetes Mellitus (collectively referred to here as Diabetes), resting heart rate, homeostatic model assessment (HOMA), HOMA insulin resistance (HOMA-IR), intravenous glucose tolerance (SI(IVGT)), β-cell function, macrovascular function, microvascular function, atherogenic index, blood pressure, low-density lipoprotein/high-density lipoprotein ratio, intima-media thickness, and UKPDS risk score. Other clinical parameters are disclosed in US Publication US/2008/0057590.

The biomarkers of the invention show a statistically significant difference between different states of cardiodiabetes. In various embodiments, diagnostic tests that use these biomarkers alone or in combination show a sensitivity and specificity of at least about 85%, at least about 90%, at least about 95%, at least about 98% and about 100%.

Measurement and Detection of Biomarkers

Biomarkers generally can be measured and detected through a variety of assays, methods and detection systems known to one of skill in the art. The term "measuring," "detecting," or "taking a measurement" refers to a quantitative or qualitative determination of a property of an entity, e.g., quantifying the amount or concentration of a molecule or the activity level of a molecule. The term "concentration" or "level" can refer to an absolute or relative quantity. Measuring a molecule may also include determining the absence or presence of the molecule. Various methods include but are not limited to refractive index spectroscopy (RI), ultra-violet spectroscopy (UV), fluorescence analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

Thus, of particular interest in the present invention are biochip assays. By "biochip" or "chip" herein is meant a composition generally comprising a solid support or substrate to which a capture binding ligand (also called an adsorbent, affinity reagent or binding ligand, or when nucleic acid is measured, a capture probe) is attached and can bind either proteins, nucleic acids or both. Generally, where a biochip is used for measurements of protein and nucleic acid biomarkers, the protein biomarkers are measured on a chip separate from that used to measure the nucleic acid biomarkers. For nonlimiting examples of additional platforms and methods useful for measuring nucleic acids, see Publications US/2006/0275782, US/2005/0064469 and DE10201463. In various embodiments, biomarkers are measured on the same platform, such as on one chip. In various embodiments, biomarkers are measured using different platforms and/or different experimental runs.

By "binding ligand," "capture binding ligand," "capture binding species," "capture probe" or grammatical equivalents herein is meant a compound that is used to detect the presence of or to quantify, relatively or absolutely, a target analyte, target species or target sequence (all used interchangeably) and that will bind to the target analyte, target species or target sequence. Generally, the capture binding ligand or capture probe allows the attachment of a target species or target sequence to a solid support for the purposes of detection as further described herein. Attachment of the target species to the capture binding ligand may be direct or indirect. In exemplary embodiments, the target species is a biomarker. As will be appreciated by those in the art, the composition of the binding ligand will depend on the composition of the biomarker. Binding ligands for a wide variety of biomarkers are known or can be readily found using known techniques. For example, when the biomarker is a protein, the binding ligands include proteins (particularly including antibodies or fragments thereof (FAbs, etc.) as discussed further below) or small molecules. The binding ligand may also have cross-reactivity with proteins of other species. Antigen-antibody pairs, receptor-ligands, and carbohydrates and their binding partners are also suitable analyte-binding ligand pairs. In various embodiments, the binding ligand may be nucleic acid. Nucleic acid binding ligands find particular use when proteins are the targets; alternatively, as is generally described in U.S. Pat. Nos. 5,270,163; 5,475,096; 5,567,588; 5,595,877; 5,637,459; 5,683,867; 5,705,337 and related patents, hereby incorporated by reference, nucleic acid "aptamers" can be developed for binding to virtually any biomarker. Nucleic acid binding ligands also find particular use when nucleic acids are binding targets. There is a wide body of literature relating to the development of binding partners based on combinatorial chemistry methods. In these embodiments, when the binding ligand is a nucleic acid, preferred compositions and techniques are outlined in PCT Publication WO/1998/020162, hereby incorporated by reference.

In various exemplary embodiments, the capture binding ligand is an antibody. These embodiments are particularly useful for the detection of the protein form of a biomarker.

Detecting or measuring the level (e.g. the transcription level) of a biomarker involves binding of the biomarker to a capture binding ligand, generally referred to herein as a "capture probe" when the mRNA of the biomarker is to be detected on a solid support. In that sense, the biomarker is a target sequence. The term "target sequence" or "target nucleic acid" or grammatical equivalents herein means a nucleic acid sequence that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. In some embodiments, measuring a nucleic acid can thus refer to measuring the complement of the nucleic acid. It may be any length, with the understanding that longer sequences are more specific.

The target sequence may also comprise different target domains; for example, a first target domain of the sample target sequence may hybridize to a first capture probe, a second target domain may hybridize to a label probe (e.g. a "sandwich assay" format), etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the target sequence, the first target domain may be located either 5' to the second domain, or 3' to the second domain.

When nucleic acids are used as the target analyte, the assays of the invention can take on a number of embodiments. In one embodiment, the assays are done in solution format, using any number of solution based formats. In one embodiment, end-point or real time PCR formats are used, as are well known in the art. These assays can be done either as a panel, in individual tubes or wells, or as multiplex assays, using sets of primers and different labels within a single tube or well. In addition to PCR-based solution formats, other formats can be utilized, including, but not limited to for example ligation based assays utilizing FRET dye pairs. In this embodiment, only upon ligation of two (or more) probes hybridized to the target sequence is a signal generated.

In many embodiments, the assays are done on a solid support, utilizing a capture probe associated with the surface. As discussed herein, the capture probes (or capture binding ligands, as they are sometimes referred to) can be covalently attached to the surface, for example using capture probes terminally modified with functional groups, for example amino groups, that are attached to modified surfaces such as silanized glass. Alternatively, non-covalent attachment, such as electrostatic, hydrophobic/hydrophilic adhesion can be utilized. As is appreciated by those in the art and discussed herein, a large number of attachments are possible on a wide variety of surfaces.

In this embodiment, the assays can take on a number of formats. In one embodiment, the target sequence comprises a detectable label, as described herein. In this embodiment, the label is generally added to the target sequence during amplification of the target in one of two ways: either labeled primers are utilized during the amplification step or labeled dNTPs are used, both of which are well known in the art. The label can either be a primary or secondary label as discussed herein. For example, in one embodiment, the label on the primer and/or a dNTP is a primary label such as a fluorophore. Alternatively, the label may be a secondary label such as biotin or an enzyme; for example, in one embodiment, the primers or dNTPs are labeled with biotin, and then a streptavidin/label complex is added. In one embodiment, the streptavidin/label complex contains a label such as a fluorophore. In an alternative embodiment, the streptavidin/label complex comprises an enzymatic label. For example, the complex can comprise horseradish peroxidase, and upon addition of TMB, the action of the horseradish peroxidase causes the TMB to precipitate, causing an optically detectable event. This has a particular benefit in that the optics for detection does not require the use of a fluorimeter.

In alternate embodiments, the solid phase assay relies on the use of a labeled soluble capture ligand, sometimes referred to as a "label probe" or "signaling probe" when the target analyte is a nucleic acid. In this format, the assay is a "sandwich" type assay, where the capture probe binds to a first domain of the target sequence and the label probe binds to a second domain. In this embodiment, the label probe can also be either a primary (e.g. a fluorophore) or a secondary (biotin or enzyme) label. In one embodiment, the label probe comprises biotin, and a streptavidin/enzyme complex is used, as discussed herein. As above, for example, the complex can comprise horseradish peroxidase, and upon addition of TMB, the action of the horseradish peroxidase causes the TMB to precipitate, causing an optically detectable event.

Detection of a target species in some embodiments requires a "label" or "detectable marker" (as described below) that can be incorporated in a variety of ways. Thus, in various embodiments, the composition comprises a "label" or a "detectable marker." In one embodiment, the target species (or target analyte or target sequence) is labeled; binding of the target species thus provides the label at the surface of the solid support.

In embodiments finding particular use herein, a sandwich format is utilized, in which target species are unlabeled. In these embodiments, a "capture" or "anchor" binding ligand is attached to the detection surface as described herein, and a soluble binding ligand (frequently referred to herein as a "signaling probe," "label probe" or "soluble capture ligand")

binds independently to the target species and either directly or indirectly comprises at least one label or detectable marker.

By "label" or "labeled" herein is meant that a compound has at least one molecule, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) enzymes; although labels include particles such as magnetic particles as well. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes and others described in the 6th Edition of the Molecular Probes Handbook by Richard P. Haugland, hereby expressly incorporated by reference. Additional labels include nanocrystals or Q-dots as described in U.S. Pat. No. 6,544,732 incorporated by reference.

In various embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc. Secondary labels can also include additional labels.

In various embodiments, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or iminobiotin) and streptavidin, digeoxinin and Abs, and Prolinx™ reagents.

In the sandwich formats of the invention, an enzyme serves as the secondary label, bound to the soluble capture ligand. Of particular use in some embodiments is the use of horseradish peroxidase, which when combined with 3,3',5,5'-tetramethylbenzidine (TMB) forms a colored precipitate which is then detected. In some cases, the soluble capture ligand comprises biotin, which is then bound to a enzyme-streptavidin complex and forms a colored precipitate with the addition of TMB.

In various embodiments, the label or detectable marker is a conjugated enzyme (for example, horseradish peroxidase). In various embodiments, the system relies on detecting the precipitation of a reaction product or on a change in, for example, electronic properties for detection. In various embodiments, none of the compounds comprises a label.

As used herein, the term "fluorescent signal generating moiety" or "fluorophore" refers to a molecule or part of a molecule that absorbs energy at one wavelength and re-emits energy at another wavelength. Fluorescent properties that can be measured include fluorescence intensity, fluorescence lifetime, emission spectrum characteristics, energy transfer, and the like.

Signals from single molecules can be generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, *Scanning Electron Microscopy: Physics of Image Formation and Microanalysis*, 2nd Edition (Springer, 1998); Nie et al, *Anal. Chem.*, 78: 1528-1534 (2006); Hecht et al, *Journal Chemical Physics*, 112: 7761-7774 (2000); Zhu et al, editors, *Near-Field Optics: Principles and Applications* (World Scientific Publishing, Singapore, 1999); Drmanac, PCT Publication WO/2004/076683; Lehr et al, *Anal. Chem.*, 75: 2414-2420 (2003); Neuschafer et al, *Biosensors & Bioelectronics*, 18: 489-497 (2003); Neuschafer et al, U.S. Pat. No. 6,289,144; and the like.

Thus, a detection system for fluorophores includes any device that can be used to measure fluorescent properties as discussed above. In various embodiments, the detection system comprises an excitation source, a fluorophore, a wavelength filter to isolate emission photons from excitation photons and a detector that registers emission photons and produces a recordable output, in some embodiments as an electrical signal or a photographic image. Examples of detection devices include without limitation spectrofluorometers and microplate readers, fluorescence microscopes, fluorescence scanners (including e.g. microarray readers) and flow cytometers.

In various exemplary embodiments, the binding of the biomarker to the binding ligand is specific or selective, and the binding ligand is part of a binding pair. By "specifically bind" or "selectively bind" or "selective for" a biomarker herein is meant that the ligand binds the biomarker with specificity sufficient to differentiate between the biomarker and other components or contaminants of the test sample.

The term "solid support" or "substrate" refers to any material that can be modified to contain discrete individual sites appropriate for the attachment or association of a capture binding ligand. Suitable substrates include metal surfaces such as gold, electrodes, glass and modified or functionalized glass, plastics (including acrylics, polystyrene and copolymers of styrene and other materials, polypropylene, polyethylene, polybutylene, polycarbonate, polyurethanes, Teflon, derivatives thereof, etc.), polysaccharides, nylon or nitrocellulose, resins, mica, silica or silica-based materials including silicon and modified silicon, carbon, metals, inorganic glasses, fiberglass, ceramics, GETEK (a blend of polypropylene oxide and fiberglass) and a variety of other polymers. Of particular use in the present invention are the ClonDiag materials described below.

Frequently, the surface of a biochip comprises a plurality of addressable locations, each of which comprises a capture binding ligand. An "array location," "addressable location," "pad" or "site" herein means a location on the substrate that comprises a covalently attached capture binding ligand. An "array" herein means a plurality of capture binding ligands in a regular, ordered format, such as a matrix. The size of the array will depend on the composition and end use of the array. Arrays containing from about two or more different capture binding ligands to many thousands can be made. Generally, the array will comprise 3, 4, 5, 6, 7 or more types of capture binding ligands depending on the end use of the array. In the present invention, the array can include controls, replicates of the markers and the like. Exemplary ranges are from about 3 to about 50. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, in one aspect, the invention provides a composition comprising a solid support comprising a capture binding ligand for each biomarker of a biomarker panel. In various embodiments, the capture binding ligand is an antibody. In various embodiments, the composition further comprises a soluble binding ligand for each biomarker of a biomarker panel.

A number of different biochip array platforms as known in the art may be used. For example, the compositions and methods of the present invention can be implemented with array platforms such as GeneChip (Affymetrix), CodeLink Bioarray (Amersham), Expression Array System (Applied Biosystems), SurePrint microarrays (Agilent), Sentrix LD BeadChip or Sentrix Array Matrix (Illumina) and Verigene (Nanosphere).

In various exemplary embodiments, detection and measurement of biomarkers utilizes colorimetric methods and systems in order to provide an indication of binding of a target analyte or target species. In colorimetric methods, the presence of a bound target species such as a biomarker will result in a change in the absorbance or transmission of light by a sample or substrate at one or more wavelengths. Detection of the absorbance or transmission of light at such wavelengths thus provides an indication of the presence of the target species.

A detection system for colorimetric methods includes any device that can be used to measure colorimetric properties as discussed above. Generally, the device is a spectrophotometer, a colorimeter or any device that measures absorbance or transmission of light at one or more wavelengths. In various embodiments, the detection system comprises a light source; a wavelength filter or monochromator; a sample container such as a cuvette or a reaction vial; a detector, such as a photoresistor, that registers transmitted light; and a display or imaging element.

In various exemplary embodiments, a ClonDiag chip platform is used for the colorimetric detection of biomarkers. In various embodiments, a ClonDiag ArrayTube (AT) is used. One unique feature of the ArrayTube is the combination of a micro probe array (the biochip) and micro reaction vial. In various embodiments, where a target sequence is a nucleic acid, detection of the target sequence is done by amplifying and biotinylating the target sequence contained in a sample and optionally digesting the amplification products. The amplification product is then allowed to hybridize with probes contained on the ClonDiag chip. A solution of a streptavidin-enzyme conjugate, such as Poly horseradish peroxidase (HRP) conjugate solution, is contacted with the ClonDiag chip. After washing, a dye solution such as o-dianisidine substrate solution is contacted with the chip. Oxidation of the dye results in precipitation that can be detected colorimetrically. Further description of the ClonDiag platform is found in Monecke S, Slickers P, Hotzel H et al., *Clin Microbiol Infect* 2006, 12: 718-728; Monecke S, Berger-Bächi B, Coombs C et al., *Clin Microbiol Infect* 2007, 13: 236-249; Monecke S, Leube I and Ehricht R, *Genome Lett* 2003, 2: 106-118; Monecke S and Ehricht R, *Clin Microbiol Infect* 2005, 11: 825-833; German Patent DE 10201463; US Publication US/2005/0064469 and ClonDiag, *ArrayTube (AT) Experiment Guideline for DNA-Based Applications*, version 1.2, 2007, all incorporated by reference in their entirety. One of skill in the art will appreciate that numerous other dyes that react with a peroxidase can be utilized to produce a colorimetric change, such as 3,3',5,5'-tetramethylbenzidine (TMB).

In various embodiments, where a target species is a protein, the ArrayTube biochip comprises capture binding ligands such as antibodies. A sample is contacted with the biochip, and any target species present in the sample is allowed to bind to the capture binding ligand antibodies. A soluble capture binding ligand or a detection compound such as a horseradish peroxidase conjugated antibody is allowed to bind to the target species. A dye, such as TMB, is then added and allowed to react with the horseradish peroxidase, causing precipitation and a color change that is detected by a suitable detection device. Further description of protein detection using ArrayTube is found in, for example, Huelseweh B, Ehricht R and Marschall H-J, *Proteomics*, 2006, 6, 2972-2981; and ClonDiag, *ArrayTube (AT) Experiment Guideline for Protein-Based Applications*, version 1.2, 2007, all incorporated by reference in their entirety.

Transmission detection and analysis is performed with a ClonDiag AT reader instrument. Suitable reader instruments and detection devices include the ArrayTube Workstation ATS and the ATR 03.

In addition to ArrayTube, the ClonDiag ArrayStrip (AS) can be used. The ArrayStrip provides a 96-well format for high volume testing. Each ArrayStrip consists of a standard 8-well strip with a microarray integrated into the bottom of each well. Up to 12 ArrayStrips can be inserted into one microplate frame enabling the parallel multiparameter testing of up to 96 samples. The ArrayStrip can be processed using the ArrayStrip Processor ASP, which performs all liquid handling, incubation, and detection steps required in array based analysis. In various embodiments, where a protein is detected, a method of using the ArrayStrip to detect the protein comprises conditioning the AS array with buffer or blocking solution; loading of up to 96 sample solutions in the AS wells to allow for binding of the protein; 3× washing; conjugating with a secondary antibody linked to HRP; 3× washing; precipitation staining with TMB; and AS array imaging and optional data storage.

Those skilled in the art will be familiar with numerous additional immunoassay formats and variations thereof which may be useful for carrying out the method disclosed herein. See generally E. Maggio, *Enzyme-Immunoassay*, (CRC Press, Inc., Boca Raton, Fla., 1980); see also U.S. Pat. Nos. 4,727,022; 4,659,678; 4,376,110; 4,275,149; 4,233,402; and 4,230,767.

In general, immunoassays carried out in accordance with the present invention may be homogeneous assays or heterogeneous assays. In a homogeneous assay the immunological reaction usually involves the specific antibody (e.g., anti-biomarker protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include immunoblotting, immunofluorescence methods, immunoprecipitation, chemiluminescence methods, electrochemiluminescence (ECL) or enzyme-linked immunoassays.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

As used herein, the term "antibody" means a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

Using any of the methods and compositions described herein, a sample can be assayed to determine levels of a biomarker panel. Thus, in one aspect, the invention provides a method of assaying a sample from a patient to determine concentrations of a biomarker panel in the sample. In some embodiments, the method comprises contacting the sample with a composition comprising a solid support comprising a capture binding ligand or capture probe for each biomarker of a biomarker panel.

The invention further provides kits for use in determining cardiodiabetes for a number of medical (including diagnostic and therapeutic), industrial, forensic and research applications. Kits may comprise a carrier, such as a box, carton, tube or the like, having in close confinement therein one or more containers, such as vials, tubes, ampoules, bottles, pouches, envelopes and the like. In various embodiments, the kits comprise one or more components selected from one or more media or media ingredients and reagents for the measurement of the various biomarkers and biomarker panels disclosed herein. For example, kits of the invention may also comprise, in the same or different containers, one or more DNA polymerases, one or more primers, one or more suitable buffers, one or more nucleotides (such as deoxynucleoside triphosphates (dNTPs) and preferably fluorescently labeled dNTPs) and labeling components. The one or more components may be contained within the same container, or may be in separate containers to be admixed prior to use. The kits of the present invention may also comprise one or more instructions or protocols for carrying out the methods of the present invention. The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semiconductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of biomarkers as provided herein. In various embodiments, the kit comprises a biomarker assay involving a lateral-flow-based point-of-care rapid test with detection of risk thresholds, or a biochip with quantitative assays for the constituent biomarkers.

Methods of Diagnosing and Treating

The compositions and methods of the present invention can be used in the prognosis, diagnosis and treatment of disease in a subject. The invention provides compositions and methods for laboratory and point-of-care tests for measuring biomarkers in a sample from a subject. The invention can be generally applied for a number of different diseases. In exemplary embodiments, the disease is cardiodiabetes. In exemplary embodiments, the disease is cardiovascular disease or risk. In exemplary embodiments, the disease is metabolic syndrome.

The biomarkers and biomarker panels disclosed herein can be used in methods to diagnose, identify or screen subjects that have, do not have or are at risk for having disease; to monitor subjects that are undergoing therapies for disease; to determine or suggest a new therapy or a change in therapy; to differentially diagnose disease states associated with the disease from other diseases or within sub-classifications of disease; to evaluate the severity or changes in severity of disease in a patient; to stage a subject with the disease and to select or modify therapies or interventions for use in treating subjects with the disease. In an exemplary embodiment, the methods of the present invention are used to identify and/or diagnose subjects who are asymptomatic or presymptomatic for a disease. In this context, "asymptomatic" or "presymptomatic" means not exhibiting the traditional symptoms or enough abnormality for disease. In exemplary embodiments, the subject is normoglycemic.

In various embodiments, a method of determining a prognosis of a disease in a subject, diagnosing a disease in a subject, or treating a disease in a subject comprises taking a measurement of a biomarker panel in a sample from the subject. In various exemplary embodiments, the biomarker panel consists of adiponectin, hsCRP and intact proinsulin.

The term "disease status" includes any distinguishable manifestation of the disease, including non-disease. For example, disease status includes, without limitation, the presence or absence of disease, the risk of developing disease, the stage of the disease, the progression of disease (e.g., progress of disease or remission of disease over time), the severity of disease and the effectiveness or response to treatment of disease.

A "subject" in the context of the present invention is an animal, preferably a mammal The mammal can be a human, non-human primate, mouse, rat, dog, cat, horse, or cow, but are not limited to these examples. In various exemplary embodiments, a subject is human and may be referred to as a patient. Mammals other than humans can be advantageously used as subjects that represent animal models of a disease or for veterinarian applications. A subject can be one who has been previously diagnosed or identified as having a disease, and optionally has already undergone, or is undergoing, a therapeutic intervention for a disease. Alternatively, a subject can also be one who has not been previously diagnosed as having a disease. For example, a subject can be one who exhibits one or more risk factors for a disease, or one who does not exhibit a disease risk factor, or one who is asymptomatic for a disease. A subject can also be one who is suffering from or at risk of developing a disease. In certain embodiments, the subject can be already undergoing therapy or can be a candidate for therapy.

As will be appreciated by those in the art, the biomarkers may be measured in using several techniques designed to achieve more predictable subject and analytical variability. On subject variability, many of the above biomarkers are commonly measured in a fasting state, commonly in the morning, providing a reduced level of subject variability due to both food consumption and metabolism and diurnal variation. All fasting and temporal-based sampling procedures using the biomarkers described herein may be useful for performing the invention. Pre-processing adjustments of biomarker results may also be intended to reduce this effect.

The term "sample" refers to a specimen or culture obtained from a subject and includes fluids, gases and solids including for example tissue. In various exemplary embodiments, the sample comprises blood. Fluids obtained from a subject include for example whole blood or a blood derivative (e.g. serum, plasma, or blood cells), ovarian cyst fluid, ascites, lymphatic, cerebrospinal or interstitial fluid, saliva, mucous, sputum, sweat, urine, or any other secretion, excretion, or other bodily fluids. As will be appreciated by those in the art, virtually any experimental manipulation or sample preparation steps may have been done on the sample. For example, wash steps and/or fragmentation may be applied to a sample. In various embodiments, a biomarker panel is measured directly in a subject without the need to obtain a separate sample from the patient.

In one aspect, the invention provides a method of diagnosing a subject for a disease comprising taking a measurement of a biomarker panel; and correlating the measurement with the disease. The term "correlating" generally refers to determining a relationship between one type of data with another or with a state. In various embodiments, correlating the measurement with disease comprises comparing the measurement with a reference biomarker profile or some other reference value. In various embodiments, correlating the measurement with disease comprises determining whether the subject is currently in a state of disease.

The quantity or activity measurements of a biomarker panel can be compared to a reference value. Differences in the measurements of biomarkers in the subject sample compared to the reference value are then identified. In exemplary embodiments, the reference value is given by a risk category as described further below.

In various embodiments, the reference value is a baseline value. A baseline value is a composite sample of an effective amount of biomarkers from one or more subjects who do not have a disease, who are asymptomatic for a disease or who have a certain level of a disease. A baseline value can also comprise the amounts of biomarkers in a sample derived from a subject who has shown an improvement in risk factors of a disease as a result of treatments or therapies. In these embodiments, to make comparisons to the subject-derived sample, the amounts of biomarkers are similarly calculated. A reference value can also comprise the amounts of biomarkers derived from subjects who have a disease confirmed by an invasive or non-invasive technique, or are at high risk for developing a disease. Optionally, subjects identified as having a disease, or being at increased risk of developing a disease are chosen to receive a therapeutic regimen to slow the progression of a disease, or decrease or prevent the risk of developing a disease. A disease is considered to be progressive (or, alternatively, the treatment does not prevent progression) if the amount of biomarker changes over time relative to the reference value, whereas a disease is not progressive if the amount of biomarkers remains constant over time (relative to the reference population, or "constant" as used herein). The term "constant" as used in the context of the present invention is construed to include changes over time with respect to the reference value.

The biomarkers of the present invention can be used to generate a "reference biomarker profile" of those subjects who do not have a disease according to a certain threshold, are not at risk of having a disease or would not be expected to develop a disease. The biomarkers disclosed herein can also be used to generate a "subject biomarker profile" taken from subjects who have a disease or are at risk for having a disease. The subject biomarker profiles can be compared to a reference biomarker profile to diagnose or identify subjects at risk for developing a disease, to monitor the progression of disease, as well as the rate of progression of disease, and to monitor the effectiveness of disease treatment modalities. The reference and subject biomarker profiles of the present invention can be contained in a machine-readable medium, such as but not limited to, analog tapes like those readable by a VCR; optical media such as CD-ROM, DVD-ROM and the like; and solid state memory, among others.

Measurements of the biomarker panels of the invention can lead a practitioner to effect a therapy with respect to a subject. Thus, the invention provides methods of treating a disease in a subject comprising taking a measurement of a biomarker panel in a sample from the subject, and effecting a therapy with respect to the subject. The terms "therapy" and "treatment" may be used interchangeably. In certain embodiments, the therapy can be selected from, without limitation, initiating therapy, continuing therapy, modifying therapy or ending therapy. A therapy also includes any prophylactic measures that may be taken to prevent disease.

In certain embodiments, therapy comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery, for example, bariatric surgery.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

Drug Treatments

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug and may include, for example, a reduction in body mass index (BMI), a reduction in total cholesterol levels, a reduction in LDL levels, an increase in HDL levels, a reduction in systolic and/or diastolic blood pressure, or combinations thereof.

A number of compounds such as a disease-modulating drug may be used to treat a subject and to monitor progress using the methods of the invention. In certain embodiments, the disease-modulating drug comprises an antiobesity drug, a β-blocker, an angiotensin-converting enzyme (ACE) inhibitor, a diuretic, a calcium channel blocker, an angiotensin II receptor blocker, an antiplatelet agent, an anti-coagulant agent, a sulfonylurea (SU), a biguanide, an insulin, a glitazone (thiazolidinedione (TZD)), a nitrate, an non-steroidal anti-inflammatory agent, a statin, cilostazol, pentoxifylline, buflomedil or naftidrofuryl. In addition, any and all combinations of these drugs may be administered.

The beneficial effects of these and other drugs can be visualized by assessment of clinical and laboratory biomarkers. For example, results from PROactive (Pfützner et al., *Expert Review of Cardiovascular Therapy*, 2006, 4: 445-459) and recent metanalyses have shown that these surrogate changes may translate into effective reduction of cardiovascular risk in patients with type 2 diabetes mellitus.

In various exemplary embodiments, a glitazone (also referred to as a thiazolidinedione (TZD)) is administered to a subject to treat a disease. The glitazones form a class of drugs that have been used to treat subjects with diabetes mellitus (type 2) and related diseases. Glitazones act by binding to PPARs (peroxisome proliferator-activated receptors), a group of receptor molecules inside the cell nucleus, specifically PPARγ (gamma) The normal ligands for these receptors are free fatty acids (FFAs) and eicosanoids. When activated, the receptor migrates to the DNA, activating transcription of a number of specific genes.

Examples of glitazones that may be useful in the present invention include, but are not limited to, rosiglitazone (Avandia™), pioglitazone (Actos™) and troglitazone (Rezulin™). Glitazones and other drugs administered to treat a subject have been shown to affect levels of various biomarkers. In various exemplary embodiments, pioglitazone is administered to a subject.

Furthermore, a glitazone such as pioglitazone may also be administered with other drugs. In various embodiments, pioglitazone is administered with a statin, including but not limited to simvastatin. In various embodiments, pioglitazone may be administered with another glitazone, such as rosiglitazone. In various embodiments, pioglitazone may be administered with an oral antidiabetic drug, including but not limited to a sulfonylurea (such as glimepiride) or a biguanide (such as metformin).

In various embodiments, a glucagon-like pepide 1 (GLP-1) analog is administered to a subject to treat a disease. Examples of GLP-1 analogs include but are not limited to exenatide and liraglutide.

In various embodiments, a dipeptidyl peptidase IV (DP-PIV) inhibitor is administered to a subject to treat a disease. Examples of DPPIV inhibitors include but are not limited to sitagliptin, vildagliptin and saxagliptin.

In various embodiments, metformin is administered to a subject to treat a disease.

In various embodiments, a glinide is administered to a subject to treat a disease. Examples of glinides include but are not limited to repgalinide and nateglinide.

In various embodiments, a sulfonylurea is administered to a subject to treat a disease. Examples of sulfonylureas include but are not limited to gliclazide and glimepiride.

In various embodiments, an α-glucosidase inhibitor is administered to a subject to treat a disease. An example of an α-glucosidase inhibitor is acarbose.

In various embodiments, an insulin is administered to a subject to treat a disease. The term "insulin" by itself refers to any naturally occurring form of insulin as well as any derivatives and analogs thereof Different types of insulin may vary in the onset, peak occurrence and duration of their effects. Examples of insulin that may be useful in the present invention include but are not limited to regular human insulin, intermediate acting regular human insulin (e.g., NPH human insulin), Zn-retarded insulin, short acting insulin analog and long acting insulin analog. Examples of Zn-retarded insulin include but are not limited to lente and ultralente. Examples of short-acting insulin analog include but are not limited to lispro, aspart and glulisine. Examples of long-acting insulin analog include but are not limited to glargine and levemir.

Any drug or combination of drugs disclosed herein may be administered to a subject to treat a disease. The drugs herein can be formulated in any number of ways, often according to various known formulations in the art or as disclosed or referenced herein.

In various exemplary embodiments, a subject is administered a glitazone and a drug or combination of drugs selected from a GLP-1 analog and an insulin. In various exemplary embodiments, a subject is administered a glitazone and a drug or combination of drugs selected from a GLP-1 analog, an insulin and a DPPIV inhibitor. In various exemplary embodiments, a subject is administered metformin and a drug or combination of drugs selected from a glitazone, a GLP-1 analog, a DPPIV inhibitor and an insulin. In various exemplary embodiments, a subject is administered metformin and a drug or combination of drugs selected from a glitazone, a DPPIV inhibitor and an insulin.

In various embodiments, a subject is administered a drug or combination of drugs selected from a glitazone, a GLP-1 analog and an insulin. In various embodiments, a subject is administered a drug or combination of drugs selected from a glitazone, a GLP-1 analog, an insulin and a DPPIV inhibitor. In various embodiments, a subject is administered a drug or combination of drugs selected from metformin, a glitazone, a GLP-1 analog, a DPPIV inhibitor and an insulin. In various embodiments, a subject is administered a drug or combination of drugs selected from metformin, a glitazone, a DPPIV inhibitor and an insulin.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various exemplary embodiments, a glinide is not administered to a subject. In various exemplary embodiments, a sulfonylurea is not administered to a subject. In various exemplary embodiments, a drug or drug combination selected from a glinide and a sulfonylurea is not administered to a subject.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more glucose lowering drugs.

In exemplary embodiments, one or more additional drugs comprise one or more glucose lowering drugs. In various embodiments, one or more additional drugs comprise one or more glucose lowering drugs comprising a drug or combination of drugs selected from a glitazone, a GLP-1 analog, a DPPIV inhibitor, metformin, a glinide, a sulfonylurea, an α-glucosidase inhibitor and an insulin. In various embodiments, the insulin is selected from a regular human insulin, an intermediate-acting regular human insulin, a Zn-retarded insulin, a short-acting insulin analog and a long-acting insulin analog. In exemplary embodiments, one or more additional drugs comprise one or more glucose lowering drugs excluding a drug or combination of drugs selected from a sulfonylurea, a glinide and a regular human insulin.

In exemplary embodiments, one or more glucose lowering drugs comprise a drug or combination of drugs selected from a DDPIV inhibitor, metformin and an α-glucosidase inhibitor. In exemplary embodiments, one or more glucose lowering drugs comprise a drug or combination of drugs selected from metformin and an α-glucosidase inhibitor. In exemplary embodiments, a glucose lowering drug is an α-glucosidase inhibitor. In exemplary embodiments, one or more glucose lowering drugs comprise a drug or combination of drugs selected from a GLP-1 analog, a glinide, a sulfonylurea and an α-glucosidase inhibitor.

In various embodiments, one or more drug is combined with one or more treatment regimens such as diet, exercise and so on.

The concept of a pathophysiological oriented therapy of type 2 diabetes with effective insulin resistance treatment shows beneficial anti-inflammatory and anti-thrombotic effects and should clearly be preferred to measures of "glucose cosmetics." Marker panels describing insulin resistance, β-cell dysfunction, adipogenesis and atherosclerosis may be more predictive and meaningful than HbA1c.

A combination of β-cell protective agents (for example, an insulin, a DPPIV inhibitor, a GLP-1 analog) might turn type 2 diabetes into a non-progressive disease. Table 5 shows the effect of a number of compounds on levels of biomarkers adiponectin, hsCRP and intact proinsulin. An up arrow indicates an increase in biomarker levels, a down arrow indicates a decrease and "O" indicates substantially no change. Thus, in one embodiment, a subject is administered a sulfonylurea, a glinide, metformin, a DPPIV-inhibitor, a GLP-1 analog, a glitazone or an insulin or combinations thereof for treatment of cardiodiabetes.

TABLE 6

|  | hsCRP | intact proinsulin | adiponectin |
|---|---|---|---|
| sulfonylurea | ↑ | ↑ | ↓ |
| glinides | ↑ | ↑ | ↓ |
| metformin | O | ↓ | ↑ |
| DPPIV-inhibitor | O | ↓ | O |
| GLP-1 analog | O | ↓ | O |
| TZD | ↓ | ↓ | ↑ |
| insulin | O | ↓ | O |

Decision Matrices

The therapy chosen by a practitioner can depend on the concentrations of biomarkers determined in a sample. In various exemplary embodiments, the therapy depends on which category from a range of categories particular to each biomarker the measured concentration of each biomarker falls in. In various exemplary embodiments, the therapy depends on the combination of risk levels for different symptoms or diseases that are indicated by a biomarker panel.

With respect to concentration measurements of a biomarker, the term "category" refers to a subset of a partition of the possible concentrations that a biomarker may have. Each category may be associated with a label or classification chosen by the practitioner. The labels may be refer to, for example, the risk level of an individual for having or being subject to a disease state. The categories and labels may be derived from the current literature or according to the findings of the practitioner. For example, it is known in the art that an individual with a serum concentration of adiponectin that is greater than 10 mg/L has a low risk for arteriosclerosis and insulin resistance, while an individual with a serum concentration of 7-10 mg/L has a medium risk for these disorders. An adiponectin concentration of greater than 10 mg/L thus can be labeled a "low risk" concentration and that of 7-10 mg/L a "medium risk" or "moderate risk" concentration. Table 2A shows that adiponectin concentrations can be divided into three categories for the purposes of the methods described herein. The number of categories and the boundaries dividing them may vary. For example, Table 2B shows an alternative categorization for adiponectin. The number of categories and the boundaries dividing them for any biomarker are not limited to those specifically disclosed herein and can be found in the art.

Each biomarker of a biomarker panel can thus be associated with a discrete set of categories, for example, risk categories. Combining one category from each biomarker forms a "decision point." In various exemplary embodiments, the complete set of decision points comprises all possible n-tuples of categories, wherein n is the number of biomarkers in the biomarker panel. This complete set will have $m_1 \times m_2 \times \ldots m_n$ possible decision points, wherein $m_i$ is the number of categories for biomarker i.

Every decision point can be associated with a condition or a disease state, which is not necessarily unique. That is, one or more decision points can be associated with the same disease state. The association of every possible decision point with a condition or disease state can be referred to as a "disease classification matrix" or a "disease classification tree." Thus, by correlating a measurement of a biomarker panel with a decision point, the practitioner can classify the condition or disease state of a patient.

Every decision point can also be associated with a particular therapy, which is not necessarily unique. That is, one or more decision points can be associated with the same therapy. The association of every possible decision point with one or more therapies can be referred to as a "therapy decision matrix" or "therapy decision tree."

Each decision point can be associated with more than one type of information. For example, both disease state and therapy can be indicated by a decision point.

In various exemplary embodiments, the biomarker panel consists of adiponectin, hsCRP and intact proinsulin. In various exemplary embodiments, possible concentrations of adiponectin in a sample are divided into 3 risk categories. In various exemplary embodiments, possible concentrations of hsCRP in a sample are divided into 3 risk categories. In various exemplary embodiments, possible concentrations of intact proinsulin in a sample are divided into 2 risk categories. In various exemplary embodiments, the therapy decision matrix consists of 18 decision points, each associated with a therapy that may or may not be unique across the set of all therapies.

In various exemplary embodiments, the risk categories for adiponectin are provided by Table 2A. In various exemplary embodiments, the risk categories for hsCRP are provided by Table 3. In various exemplary embodiments, the risk categories for intact proinsulin are provided by Table 4.

In various exemplary embodiments, if the risk level associated with each of the concentrations of adiponectin, hsCRP and intact proinsulin in a sample respectively is selected from (a) high, high and high; (b) high, medium and high; (c) medium, high and high; (d) low, high and high; (e) low, medium and high; and (f) low, low and high, then the subject is administered a glitazone and a drug or combination of drugs selected from a GLP-1 analog and an insulin. In various exemplary embodiments, the subject is not administered a drug or combination of drugs selected from a sulfonylurea and a glinide. In various exemplary embodiments, the subject is optionally administered one or more glucose lowering drugs. In various exemplary embodiments, the subject is optionally administered one or more glucose lowering drugs comprising a drug or combination of drugs selected from a DDPIV inhibitor, metformin and an α-glucosidase inhibitor.

In various exemplary embodiments, if the risk level associated with each of the concentrations of adiponectin, hsCRP and intact proinsulin in a sample respectively is selected from (a) high, low and high; (b) medium, medium and high; and (c) medium, low and high, then the subject is administered a glitazone and a drug or combination of drugs selected from a GLP-1 analog, an insulin and a DPPIV inhibitor. In various exemplary embodiments, the subject is not administered a drug or combination of drugs selected from a sulfonylurea and a glinide. In various exemplary embodiments, the subject is optionally administered one or more glucose lowering drugs. In various exemplary embodiments, the subject is optionally administered one or more glucose lowering drugs comprising a drug or combination of drugs selected from metformin and an α-glucosidase inhibitor.

In various exemplary embodiments, if the risk level associated with each of the concentrations of adiponectin, hsCRP and intact proinsulin in a sample respectively is selected from (a) high, high and low; (b) medium, high and low; (c) low, high and low; (d) low, medium and low; and (e) low, low and low, then the subject is administered metformin and a drug or combination of drugs selected from a glitazone, a GLP-1 analog, a DPPIV inhibitor and an insulin. In various exemplary embodiments, the subject is not administered a drug or combination of drugs selected from a sulfonylurea and a glinide. In various exemplary embodiments, the subject is optionally administered one or more glucose lowering drugs. In various exemplary embodiments, the subject is optionally administered a glucose lowering drug comprising an α-glucosidase inhibitor.

In various exemplary embodiments, when the concentration of adiponectin in a sample from a subject is if the risk level associated with each of the concentrations of adiponectin, hsCRP and intact proinsulin in a sample respectively is selected from (a) high, medium and low; (b) high, low and low; (c) medium, medium and low; and (d) medium, low and low, then the therapy comprises administering metformin and a drug or combination of drugs selected from a glitazone, a DPPIV inhibitor and an insulin. In various exemplary embodiments, the subject is optionally administered one or more glucose lowering drugs. In various exemplary embodiments, the subject is optionally administered one or more glucose lowering drugs comprising a drug or combination of drugs selected from a GLP-1 analog, a glinide, a sulfonylurea and an α-glucosidase inhibitor.

In one aspect, the invention provides drugs for the treatment of a disease. In exemplary embodiments, these drugs are administered to a subject for which concentrations of each biomarker of a biomarker panel in a sample from the subject correspond to a decision point provided herein.

In various embodiments, the drugs comprise a glitazone and a drug or combination of drugs selected from a GLP-1 analog and an insulin for treating a disease in a subject for which concentrations of a biomarker panel in a sample from the subject are measured. In various exemplary embodiments, the biomarker panel consists of adiponectin, hsCRP and intact proinsulin, and the risk level associated with each of the concentrations of adiponectin, hsCRP and intact proinsulin respectively is selected from (a) high, high and high; (b) high, medium and high; (c) medium, high and high; (d) low, high and high; (e) low, medium and high; and (f) low, low and high. In various exemplary embodiments, the drugs do not include a drug or combination of drugs selected from a sulfonylurea and a glinide. In various exemplary embodiments, the drugs optionally further comprise one or more additional drugs selected from one or more glucose lowering drugs. In various exemplary embodiments, one or more glucose lowering drugs comprise a drug or combination of drugs selected from a DPPIV inhibitor, metformin and an α-glucosidase inhibitor.

In various embodiments, the drugs comprise a glitazone and a drug or combination of drugs selected from a GLP-1 analog, an insulin and a DPPIV inhibitor for treating a disease in a subject for which concentrations of a biomarker panel in a sample from the subject are measured. In various exemplary embodiments, the biomarker panel consists of adiponectin, hsCRP and intact proinsulin, and the risk level associated with each of the concentrations of adiponectin, hsCRP and intact proinsulin respectively is selected from (a) high, low and high; (b) medium, medium and high; and (c) medium, low and high. In various exemplary embodiments, the drugs do not include a drug or combination of drugs selected from a sulfonylurea and a glinide. In various exemplary embodiments, the drugs optionally further comprise one or more additional drugs selected from one or more glucose lowering drugs. In various exemplary embodiments, one or more glucose lowering drugs comprise a drug or combination of drugs selected from metformin and an α-glucosidase inhibitor.

In various embodiments, the drugs comprise metformin and a drug or combination of drugs selected from a glitazone, a GLP-1 analog, a DPPIV inhibitor and an insulin for treating a disease in a subject for which concentrations of a biomarker panel in a sample from the subject are measured. In various exemplary embodiments, the biomarker panel consists of adiponectin, hsCRP and intact proinsulin, and the risk level associated with each of the concentrations of adiponectin, hsCRP and intact proinsulin respectively is selected from (a) high, high and low; (b) medium, high and low; (c) low, high and low; (d) low, medium and low; and (e) low, low and low. In various exemplary embodiments, the drugs do not include a drug or combination of drugs selected from a sulfonylurea and a glinide. In various exemplary embodiments, the drugs optionally further comprise one or more additional drugs selected from one or more glucose lowering drugs. In various exemplary embodiments, one or more glucose lowering drugs comprise one or more glucose lowering drugs comprising a drug or combination of drugs selected from metformin and an α-glucosidase inhibitor.

In various embodiments, the drugs comprise metformin and a drug or combination of drugs selected from a glitazone, a DPPIV inhibitor and an insulin for treating a disease in a subject for which concentrations of a biomarker panel in a sample from the subject are measured. In various exemplary embodiments, the biomarker panel consists of adiponectin, hsCRP and intact proinsulin, and the risk level associated with each of the concentrations of adiponectin, hsCRP and intact proinsulin respectively is selected from (a) high, medium and low; (b) high, low and low; (c) medium, medium and low; and (d) medium, low and low. In various exemplary embodiments, the drugs optionally further comprise one or more additional drugs selected from one or more glucose lowering drugs. In various exemplary embodiments, one or more glucose lowering drugs comprise one or more glucose lowering drugs comprising a drug or combination of drugs selected from a GLP-1 analog, a glinide, a sulfonylurea and an α-glucosidase inhibitor.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-limiting examples.

All references, publications, patent applications, issued patents, accession records and databases cited herein, including in any appendices, are incorporated by reference in their entirety for all purposes.

We claim:

1. A method of treating cardiodiabetes in a normoglycemic subject comprising:
    (a) measuring the concentration of a biomarker panel in a sample from the subject, the biomarker panel consisting of adiponectin, high sensitivity C-reactive protein (hsCRP) and intact proinsulin; and
    (b) determining a risk level associated with each biomarker,
    wherein an adiponectin concentration of >10 mg/L, 7-10 mg/L and <7 mg/L indicates a low, medium and high risk level, respectively, for adiponectin;
    an hsCRP concentration of 0-1 mg/L, >1-3 mg/L and >3-10 mg/L indicates a low, medium and high risk level, respectively, for hsCRP; and
    an intact proinsulin concentration of ≦11 pmol/L and >11 pmol/L indicates a low and high risk level, respectively, for intact proinsulin;
    (c) comparing the concentrations to each of the risk levels; and
    (d) effecting a therapy with respect to the subject, wherein in the therapy is based on a combination of the risk levels.

2. The method of claim 1 wherein if the risk level associated with each of the concentrations of adiponectin, hsCRP and intact proinsulin respectively is selected from (a) high, high and high; (b) high, medium and high; (c) medium, high and high; (d) low, high and high; (e) low, medium and high; and (f) low, low and high, then the subject is administered a glitazone and a drug or combination of drugs selected from a glucagon-like peptide 1 (GLP-1) analog and an insulin.

3. The method of claim 1 wherein if the risk level associated with each of the concentrations of adiponectin, hsCRP and intact proinsulin respectively is selected from (a) high, low and high; (b) medium, medium and high; and (c) medium, low and high, then the subject is administered a glitazone and a drug or combination of drugs selected from a GLP-1 analog, an insulin and a dipeptidyl peptidase IV (DPPIV) inhibitor.

4. The method of claim 1 if the risk level associated with each of the concentrations of adiponectin, hsCRP and intact proinsulin respectively is selected from (a) high, high and low; (b) medium, high and low; (c) low, high and low; (d) low, medium and low; and (e) low, low and low, then the subject is administered metformin and a drug or combination of drugs selected from a glitazone, a GLP-1 analog, a DPPIV inhibitor and an insulin.

5. The method of claim 1 wherein if the risk level associated with each of the concentrations of adiponectin, hsCRP and intact proinsulin respectively is selected from (a) high, medium and low; (b) high, low and low; (c) medium, medium and low; and (d) medium, low and low, then the therapy comprises administering metformin and a drug or combination of drugs selected from a glitazone, a DPPIV inhibitor and an insulin.

6. The method of any of claims 1-4 wherein the subject is not administered a drug or combination of drugs selected from a sulfonylurea and a glinide.

7. The method of any of claims 1-5 wherein the subject is administered one or more additional drugs comprising one or more glucose lowering drugs.

8. The method of claim 1 wherein the sample comprises blood.

9. The method of claim 1 further comprising taking a measurement of at least one additional biomarker.

10. The method of claim 9 wherein the additional biomarker is selected from the group consisting of leptin, mRNAx, NFκB, IL-6, MMP-9, TNFα, eNOS, PPARγ, MCP-1, PAI-1, ICAM/VCAM, E-selectin, P-selectin, von Willebrand factor, sCD40L, insulin, glucose, HbA1c, free fatty acids, triglycerides, VLDL, small dense LDL, oxidized LDL, resistin, HDL, NO, IκB-α, IκB-β, p105, RelA, TNFα, MIF, inflammatory cytokines and molecules involved in signaling pathways.

11. The method of claim 10 wherein the additional biomarker is MMP-9.

12. The method of claim 11 wherein the concentration of intact proinsulin, hsCRP and adiponectin in the sample is measured and each is a high risk concentration.

13. The method of claim 10 wherein the additional biomarker is leptin.

14. The method of claim 1 further comprising:
contacting the sample from the subject with the a composition comprising a solid support comprising:
(a) a capture binding ligand selective for adiponectin,
(b) a capture binding ligand selective for hsCRP, and
(c) a capture binding ligand selective for intact proinsulin.

* * * * *

UNITED STATES PATENT AND TRADEMARK OFFICE
CERTIFICATE OF CORRECTION

PATENT NO. : 8,383,585 B2  
APPLICATION NO. : 12/505433  
DATED : February 26, 2013  
INVENTOR(S) : Andreas Pfuetzner et al.

Page 1 of 1

It is certified that error appears in the above-identified patent and that said Letters Patent is hereby corrected as shown below:

In the Claims:

Claim 1, line 14, column 32: please delete the word "in" following "wherein."

Signed and Sealed this  
Fourteenth Day of May, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,383,585 B2
APPLICATION NO. : 12/505433
DATED : February 26, 2013
INVENTOR(S) : Andreas Pfuetzner et al.

Page 1 of 1

It is certified that error appears in the above-identified patent and that said Letters Patent is hereby corrected as shown below:

In the Claims:

Column 32, line 26 (claim 1, line 21): please delete the word "in" before "the therapy"

This certificate supersedes the Certificate of Correction issued May 14, 2013.

Signed and Sealed this
Eleventh Day of June, 2013

Teresa Stanek Rea
*Acting Director of the United States Patent and Trademark Office*